(12) United States Patent
Brown et al.

(10) Patent No.: US 7,324,918 B1
(45) Date of Patent: Jan. 29, 2008

(54) FORECASTING OUTCOMES BASED ON ANALYSIS OF TEXT STRINGS

(75) Inventors: Philip E. Brown, Westfield, NJ (US); Colin Goodall, Rumson, NJ (US); Sylvia Halasz, Fair Haven, NJ (US)

(73) Assignee: AT&T Corp, New York, NY (US)

( * ) Notice: Subject to any disclaimer, the term of this patent is extended or adjusted under 35 U.S.C. 154(b) by 210 days.

(21) Appl. No.: 11/275,430

(22) Filed: Dec. 30, 2005

(51) Int. Cl.
*G06F 19/00* (2006.01)

(52) U.S. Cl. .................... 702/181; 714/25; 600/300

(58) Field of Classification Search ............ 702/181, 702/179, 182–185, 188; 714/25, 48; 600/300
See application file for complete search history.

(56) References Cited

U.S. PATENT DOCUMENTS

| | | | |
|---|---|---|---|
| 4,872,122 A | 10/1989 | Altschuler et al. | |
| 6,609,523 B1 | 8/2003 | Anthony | |
| 2002/0107824 A1 | 8/2002 | Ahmed | |
| 2004/0103001 A1 | 5/2004 | Mazar et al. | |
| 2006/0069955 A1* | 3/2006 | Oka et al. | 714/25 |
| 2006/0190308 A1* | 8/2006 | Janssens et al. | 705/5 |

OTHER PUBLICATIONS

C.A. Mikosz, et al., Comparison of Two Major Emergency Department-Based Free-Text Chief-Complaint Coding Systems, CDC-MMWR Supplement, Sep. 24, 2004 ; pp. 1-8.

* cited by examiner

*Primary Examiner*—Edward Raymond

(57) ABSTRACT

A method and a processing device are provided for forecasting whether a record of data for an individual is associated with an outcome. Whether an n-gram associated with one of a group of predictors matches an n-gram included in the record of data is determined. When the n-gram included with the one of the group of predictors matches the n-gram in the record of data, a prediction is made as to whether the record of data is associated with the outcome based on a value assigned to the one of the group of predictors.

22 Claims, 12 Drawing Sheets

FORECASTING OUTCOMES BASED ON ANALYSIS OF TEXT STRINGS

BACKGROUND OF THE INVENTION

1. Field of the Invention

The present invention relates to forecasting an outcome based on an n-gram found in a text string and more specifically to a system and method for generating a classifier to forecast an outcome and a system and method for using the generated classifier.

2. Introduction

The public and private health sector has been investigating different approaches to disease outbreak detection using automated syndromic surveillance systems. In such systems, patient chief complaint data is collected by medical staff in an emergency department or outpatient clinic. The medical staff typically enter the patient chief complaint data in free-form text to be stored in electronic records. An automated syndromic surveillance system may perform natural language processing to analyze the free-text of the patient chief complaint data. Further, various automated syndromic surveillance systems code and prioritize symptoms differently. Thus, a syndrome profile for a group of patients may vary depending on a definition used by the automated syndromic surveillance system in a given clinical setting.

Existing automated syndromic surveillance systems suffer from a number of problems. Changes to a system may be time consuming and expensive. Because of the time involved to make changes, a practical size limit for a training set is imposed. New languages or dialects may require development of new programs for automated syndromic surveillance systems. Further, some automated syndromic surveillance system may require preprocessing of chief complaint data.

The International Classification of Diseases (ICD) coding system is an international classification system which groups related disease entities and procedures for the purpose of reporting statistical information. ICD version 9 (ICD9) and ICD version 10 (ICD10) are widely used codes. The purpose of the ICD code is to provide a uniform language and thereby serve as an effective means for reliable nationwide communication among physicians, patients, and third parties. Several days may pass from the time that a patient's chief complaint data is recorded, on first entering an emergency or urgent care department, to the time that ICD diagnoses are given. One or more ICD9 or ICD10 diagnosis codes may be assigned by medical professionals based on their diagnoses of the patient's condition, using a combination of inputs including physician notes, patient vital signs, laboratory test results, and medical examination results. (Unfortunately, assignment of ICD9 or ICD10 diagnosis codes may also be influenced by treatment and payment options.) The patient's chief complaint may provide an early indication of these diagnoses.

SUMMARY OF THE INVENTION

Additional features and advantages of the invention will be set forth in the description which follows, and in part will be obvious from the description, or may be learned by practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth herein.

In a first aspect of the invention, a method is provided for forecasting whether a record of data for an individual is associated with an outcome. Whether an n-gram associated with one of a group of predictors matches an n-gram included in the record of data is determined. When the n-gram associated with the one of the group of predictors matches the n-gram in the record of data, a prediction is made as to whether the record of data is associated with the outcome based on a value assigned to the one of the group of predictors.

In a second aspect of the invention, a machine-readable medium is provided which has recorded thereon a group of instructions for at least one processor. The machine-readable medium includes instructions for determining a group of n-grams included in a record of data, instructions for incrementing a respective record counter associated with each of the plurality of n-grams included in the record of data, instructions for determining whether the record of data is associated with an outcome of interest based, at least in part, on data associated with the record of data indicative of one or more outcomes, instructions for incrementing a respective outcome counter associated with each of the plurality of n-grams included in the record of data when the record of data is determined to be associated with the outcome of interest, instructions for repeating the previous four sets of instructions for each of a group of records of data, and instructions for assigning a value to each of the n-grams based on a value of the respective outcome counter for and a value of a corresponding record counter for the respective n-gram.

In a third aspect of the invention, a processing device is provided. The processing device includes at least one processor, a storage component having a group of instructions stored therein, and a communications interface arranged to permit communications between the at least one processor and the storage component. The at least one processor is arranged to determine a group of n-grams included in a record of data, increment a respective record counter associated with each of the group of n-grams included in the record of data, determine whether the record of data is associated with an outcome of interest based, at least in part, on data associated with the record of data indicative of one or more outcomes, increment a respective outcome counter associated with each of the group of n-grams included in the record of data when the record of data is determined to be associated with the outcome of interest, repeat the previous four acts for each of a group of records of data, and assign a value to each of the n-grams based on a value of the respective outcome counter and a value of a corresponding record counter for the respective n-gram.

In a fourth aspect of the invention, a processing device is provided for predicting whether a record of data for an individual is associated with an outcome. The processing device includes means for determining whether an n-gram associated with one of a plurality of predictors matches an n-gram included in the record of data, and means for predicting whether the record of data is associated with the outcome based on a value assigned to the one of the plurality of predictors, when the n-gram associated with the one of the plurality of predictors matches the n-gram in the record of data.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Various embodiments of the invention are discussed in detail below. While specific implementations are discussed, it should be understood that this is done for illustration purposes only. A person skilled in the relevant art will recognize that other components and configurations may be used without parting from the spirit and scope of the invention.

Exemplary System

Figure 1:
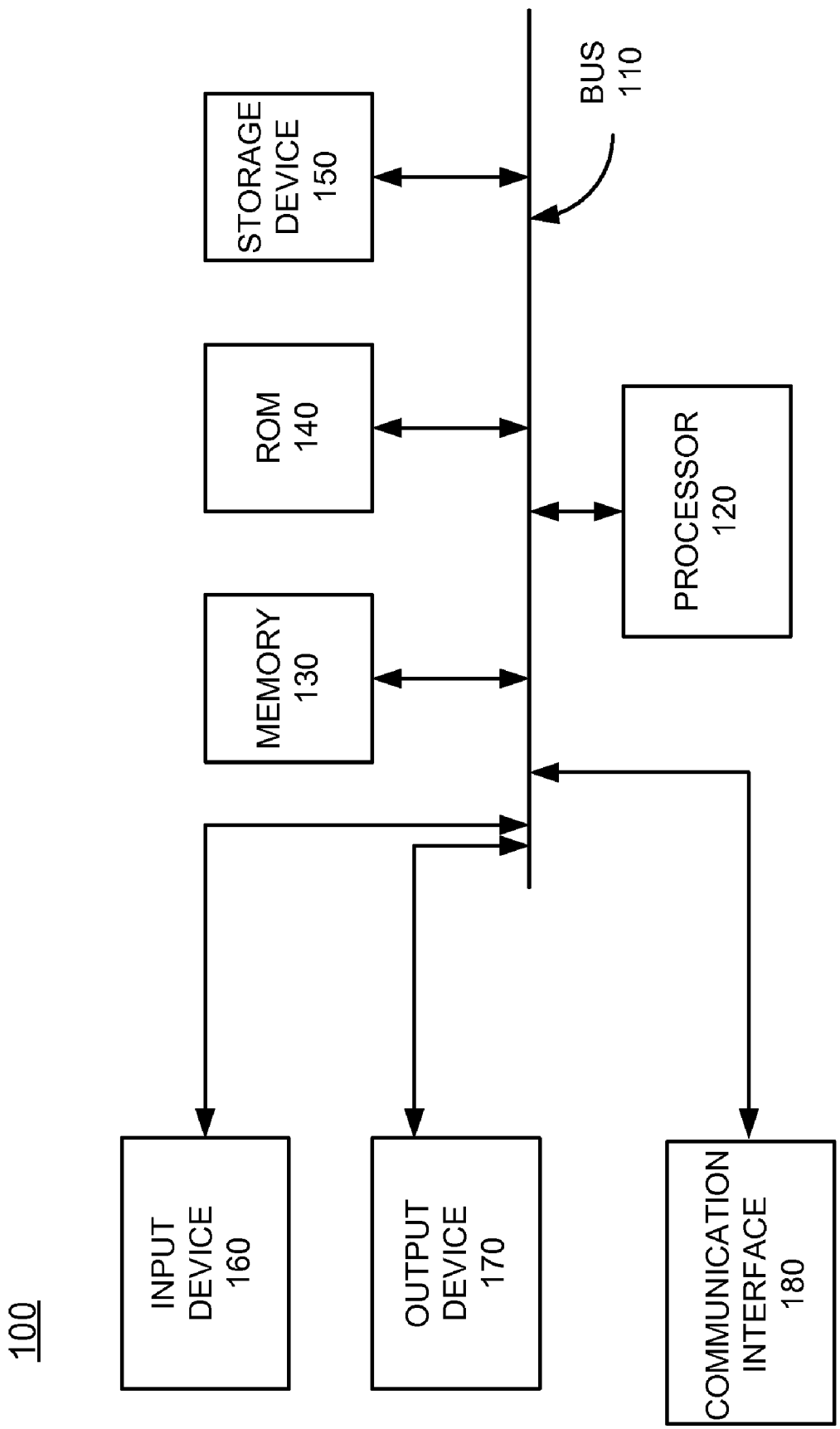
FIG. 1 illustrates an exemplary processing device in which implementations consistent with principles of the invention may execute.

FIG. 1 illustrates a block diagram of an exemplary processing device 100 which may be used to implement systems and methods consistent with the principles of the invention. Processing device 100 may include a bus 110, a processor 120, a memory 130, a read only memory (ROM) 140, a storage device 150, an input device 160, an output device 170, and a communication interface 180. Bus 110 may permit communication among the components of processing device 100.

Processor 120 may include at least one conventional processor or microprocessor that interprets and executes instructions. Memory 130 may be a random access memory (RAM) or another type of dynamic storage device that stores information and instructions for execution by processor 120. Memory 130 may also store temporary variables or other intermediate information used during execution of instructions by processor 120. ROM 140 may include a conventional ROM device or another type of static storage device that stores static information and instructions for processor 120. Storage device 150 may include any type of media, such as, for example, magnetic or optical recording media and its corresponding drive. In some implementations consistent with the principles of the invention, storage device 150 may store and retrieve data according to a database management system.

Input device 160 may include one or more conventional mechanisms that permit a user to input information to system 200, such as a keyboard, a mouse, a pen, a voice recognition device, a microphone, a headset, etc. Output device 170 may include one or more conventional mechanisms that output information to the user, including a display, a printer, one or more speakers, a headset, or a medium, such as a memory, or a magnetic or optical disk and a corresponding disk drive. Communication interface 180 may include any transceiver-like mechanism that enables processing device 100 to communicate via a network. For example, communication interface 180 may include a modem, or an Ethernet interface for communicating via a local area network (LAN). Alternatively, communication interface 180 may include other mechanisms for communicating with other devices and/or systems via wired, wireless or optical connections.

Processing device 100 may perform such functions in response to processor 120 executing sequences of instructions contained in a computer-readable medium, such as, for example, memory 130, a magnetic disk, or an optical disk. Such instructions may be read into memory 130 from another computer-readable medium, such as storage device 150, or from a separate device via communication interface 180.

Processing device 100 may be, for example, a personal computer (PC), or any other type of processing device capable of processing textual data. In alternative implementations, such as, for example, a distributed processing implementation, a group of processing devices 100 may communicate with one another via a network such that various processors may perform operations pertaining to different aspects of the particular implementation.

Generating a Predictive Model

Figure 2A:
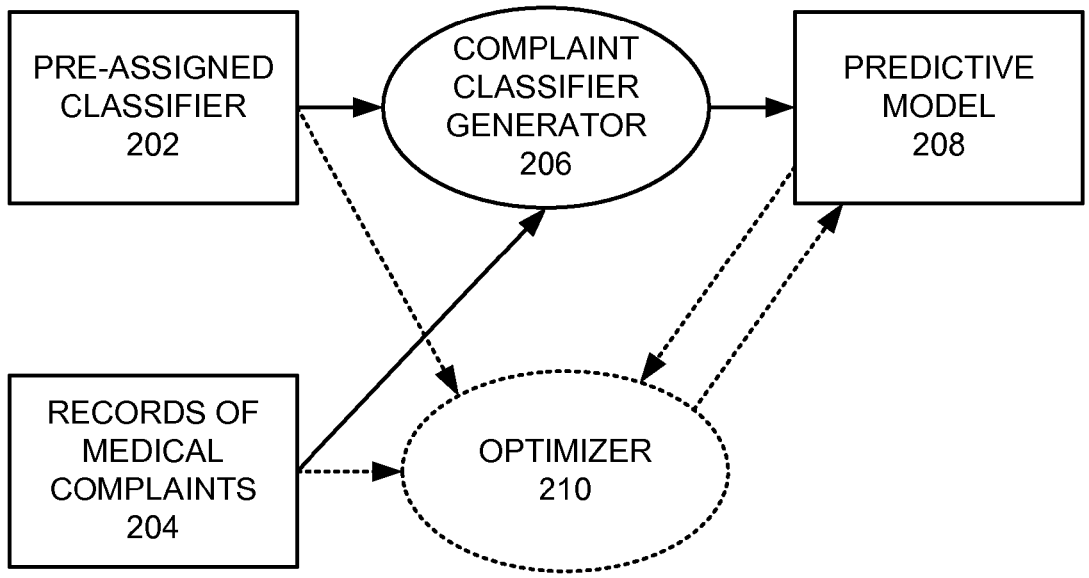
FIGS. 2A and 2B are diagrams illustrating high level views of aspects of implementations consistent with the principles of the invention.

FIG. 2A illustrates portions of an exemplary system, which may be used to build a predictive model for an automated syndromic surveillance system or other predictive outcome system, consistent with the principles of the invention. The system may include a pre-assigned classifier 202, records of medical complaints 204, a complaint classifier generator 206, a predictive model 208, which may be generated by the system, and optionally, an optimizer 210.

In one implementation consistent with the principles of the invention, pre-assigned classifier 202 may include ICD codes that have been assigned to each of the records of medical complaint data 204 by a medical professional. The ICD codes may be, for example, ICD9 or ICD 10 codes. ICD codes are well defined and may have a well-defined mapping to an outcome. An outcome may be, for example, a syndrome, a diagnosis, or any other information that indicates a result or conclusion. In alternative implementations consistent with the principles of the invention, pre-assigned classifier 202 may, instead, be data indicating a particular outcome or may be a combination of various data items that are indicative of a particular outcome, such as, for example, ICD code, patient age, patient gender, and geographic location. Each one of records of medical complaints 204 may include textual data, such as, for example, free-form alphanumeric textual characters that describe a patient's chief complaint. In addition to including alphabetic and numeric character data, the free-form alphanumeric textual characters may include spaces as well as punctuation and special characters, such as "/", "$", "@", as well as other characters.

Complaint classifier generator 206 may input each one of records of medical complaints 204, or alternatively, other text strings that may be available in patients' records. Although, for the sake of simplifying the description of implementations consistent with principles of the invention, records of medical complaint data 204 will be described as the text sting source for the following implementations of complaint classifier generator 204.

Based on n-grams appearing in respective ones of records of medical complaints 204, and further based on an associated pre-assigned classifier 202, complaint classifier generator 206 may generate predictors for predictive model 208. Each predictor may be associated with an n-gram, an outcome, and a value indicating an expected probability of an outcome associated with a predictor.

The exemplary system may include optional optimizer 210. In implementations consistent with the principles of the invention, optimizer 210 may prune predictors associated with n-grams that occur in fewer than a specific number of records of medical complaints 204 from predictive model 208. Such pruning may result in a more compact predictive model 208 and a more efficient complaint classifier. In some implementations consistent with the principles of the invention, the above-mentioned specific number of records is configurable. In one implementation consistent with the principles of the invention, predictors associated with n-grams appearing in fewer than 100 records of medical complaint data 204, may be pruned. In an alternative implementation consistent with the principles of the invention, predictors associated with n-grams appearing in fewer than a specific percentage of records may be pruned. The specific percentage may be configurable.

Figure 2B:
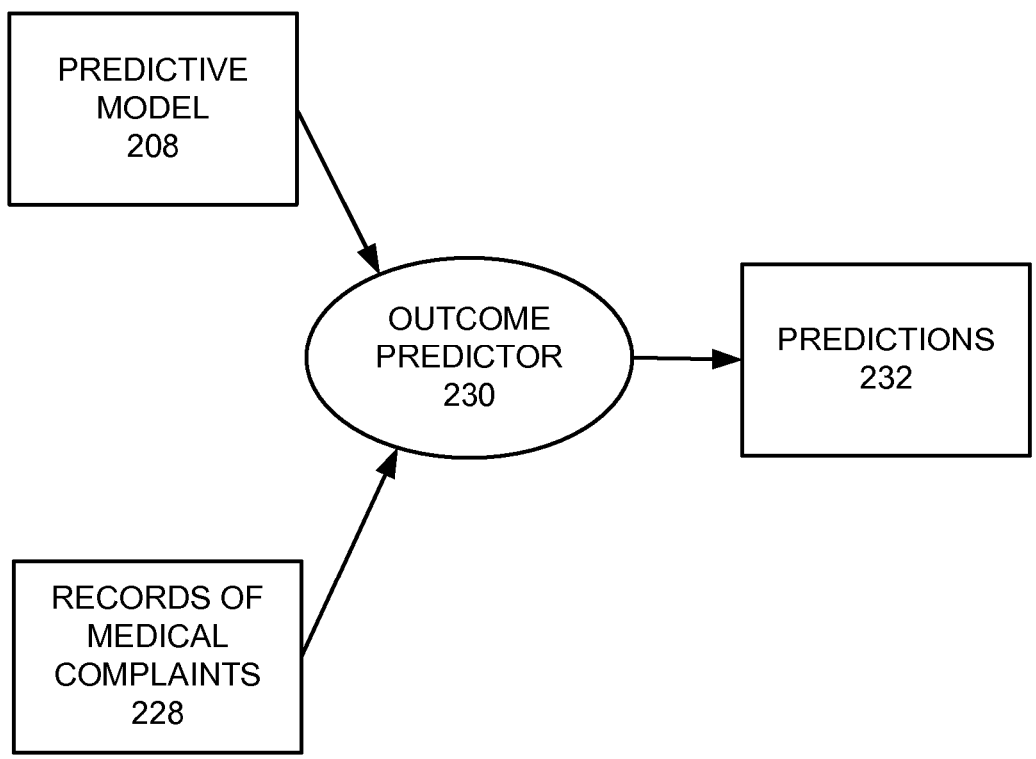

FIG. 2B is a diagram that illustrates exemplary operation of an exemplary system that may use predictive model 208 created by the exemplary system of FIG. 2A. The exemplary system may include newly received records of medical complaints 228, predictive model 208, outcome predictor 230 and predictions 232.

Newly received records of medical complaints 228 may be input by outcome predictor 230, which may use predictive model 208, created by the exemplary system of FIG. 2A. Alternatively, instead of using records of medical complaint data 228, other text strings may be available in patients' records. Although, for the sake of simplifying the description of implementations consistent with principles of the invention, we describe the source of text as newly received records of medical complaint data 228.

Using predictive model 208, outcome predictor 230 may generate one or more predictions 232 for each one of records of medical complaints 228. The one or more predictions 232 may simply state one outcome, or one or more outcomes, each with a value indicating an expected probability of a corresponding outcome. Alternatively, outcome predictor 230 may produce an expected probability, for example, a value between 0 and 1, inclusive, associated with a corresponding outcome.

Figure 3:
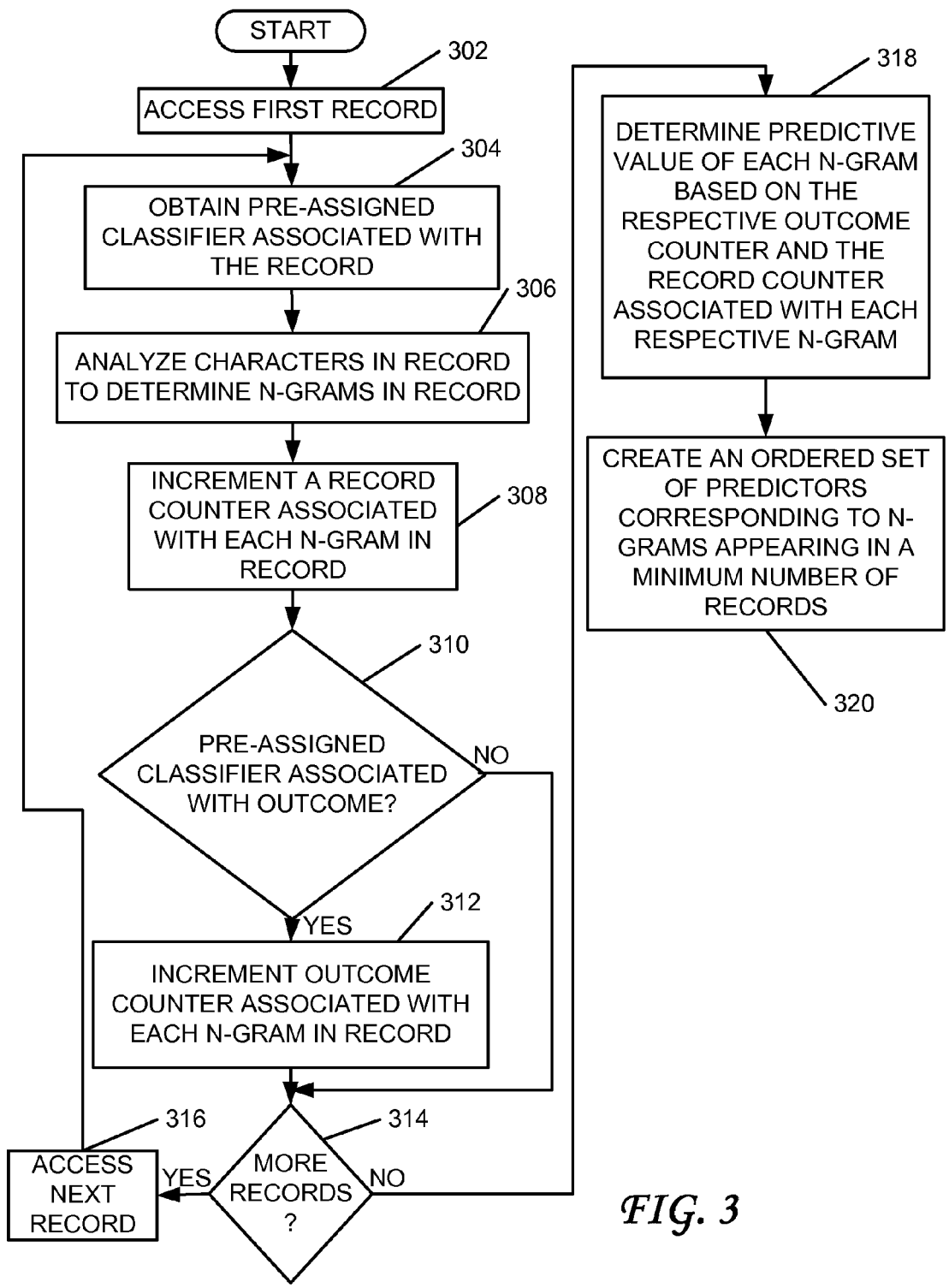
FIG. 3 is a flowchart of an exemplary process that may be performed by an implementation of a complaint classifier generator shown in FIG. 2A.

FIG. 3 is a flowchart of an exemplary process that may be employed in implementations of complaint classifier generator 206 consistent with the principles of the invention. In the exemplary process described in FIG. 3, predictors for one outcome may be generated for predictive model 208.

The process may begin with complaint classifier generator 206 accessing a first one of records of medical complaints 204, which, in this exemplary process, is being used as training data (act 302). Next, complaint classifier generator 204 may obtain a corresponding classifier from pre-assigned classifier 202 (act 304). The corresponding classifier may, but need not be included in records of medical complaints 204. Complaint classifier generator 206 may then analyze characters in the accessed one of records medical complaints 204 to determine n-grams appearing in the record (act 306). Theoretically, the n-grams may include any number of characters. Experimentation has been performed with n being 2 characters to 7 characters. A modal value of 4 for n appears to work well for English language text. Although, at least in some implementations consistent with the principles of the invention, all n-grams may not have the same length.

Assuming that n is 4, complaint classifier generator 206 may analyze the text of the record for 4-grams. Before analyzing the text, complaint classifier 206 may replace special characters, such as, for example, punctuation, "/", or other special characters with a delimiter, such as, for example, a space. A word may be defined as one or more consecutive characters preceded by a delimiter, such as, for example, a space or a beginning of a record and followed by a delimiter or end of record, with no intermediate delimiters between characters. Words having fewer than n characters (4 for this example) may be included among the n-grams, or, in this example, 4-grams. A word larger than n characters may form a number of n-grams beginning with the first through $n^{th}$ characters, second through $(n+1)^{st}$ characters, etc. For example, if a record of a medical complaint includes the following: "chest pain+wheezing", the 4-grams that may be produced are: "ches", "hest", "pain", "whee", "heez", "eezi", "ezin" and "zing". In some implementations consistent with the principles of the invention, contextual information may be stored with an n-gram. The contextual information may indicate a beginning of a word and an end of a word. For example, the 4-grams produced above, may be stored as "$_b$ches", "hest$_b$", "$_b$whee", "heez", eezi", ezin" and "zing$_b$", where "$_b$" indicates a beginning or end of a word. In some implementations, contextual information only for beginnings of words are stored. In other implementations, contextual information for only endings of words are stored.

In implementations for use with other languages, a word may be defined differently depending on a type of word delimiter used in a particular language. In one implementation consistent with the principles of the invention, a text string search may categorize each character as 1) a word character, 2) a non-word character used to define word boundaries, and 3) mapped characters, where a mapped character may be mapped to a space or an empty string (which, in effect, is character deletion). Perl is a programming language especially designed for processing text. In an embodiment of the invention, a process for performing a text string search may be programmed in Perl, which defines a word boundary as \w\W, \W\w, ^\w, \w$, where \w and \W refer to a word and non-word character, respectively, and ^ and $ are, respectively, the start and end of the text string. In other implementations, other programming languages may be used to program a text string search.

After performing act 306, complaint classifier generator 206 may increment a record counter associated with each n-gram appearing in the one of records of medical complaints 204, indicating that the corresponding n-gram was observed in a record of medical complaint data (act 308).

Next, because preassigned classifier 202 may be data indicative of an outcome, complaint classifier generator 206 may determine whether the corresponding classifier is associated with the possible outcome (act 310). If complaint classifier generator 206 determines that the corresponding classifier is associated with a particular outcome, then complaint classifier generator 206 may increment an outcome counter associated with each n-gram in the one of records of medical complaints 204 (act 312). The outcome counter for a particular n-gram keeps track of a number of records associated with the particular outcome in which the n-gram appeared.

After determining that a predefined classifier is not associated with the particular outcome (act 310), or after incrementing the corresponding outcome counters (act 312), complaint classifier generator 206 may determine whether any additional records of medical complaints 204 are to be analyzed (act 314). If there are additional records of medical complaint 204 to analyze, complaint classifier generator 206 may access the next one of records of medical complaints 204 and may again perform acts 304-314.

If, at act 314, complaint classifier generator 206 determines that there are no more records of medical complaints 204 to analyze, complaint classifier generator 206 may determine a respective predictive value to be associated with each n-gram (act 318). The value may be based on the respective outcome counter and the record counter associated with each respective n-gram. This can be expressed mathematically for each n-gram as:

$$\text{predictive value} = (\text{outcome counter}) / (\text{record counter associated with n-gram}) \quad \text{(Eq. 1)}$$

That is, complaint classifier generator 206 may calculate the predictive value corresponding to an n-gram being associated with the particular outcome by dividing the outcome counter associated with the particular n-gram by the record counter associated with the particular n-gram. The result may be a value between 0 and 1, inclusive, that may be used as an expected probability of a record of medical complaint, including the particular n-gram, being associated with the particular outcome.

Next, the results may be arranged as an ordered set of predictors (act 320). Each predictor may include an n-gram and a predictive value. The ordered set of predictors may be arranged in descending order based on the predictive values associated with the predictors. Each n-gram may appear only once in the ordered set.

Figure 4A:
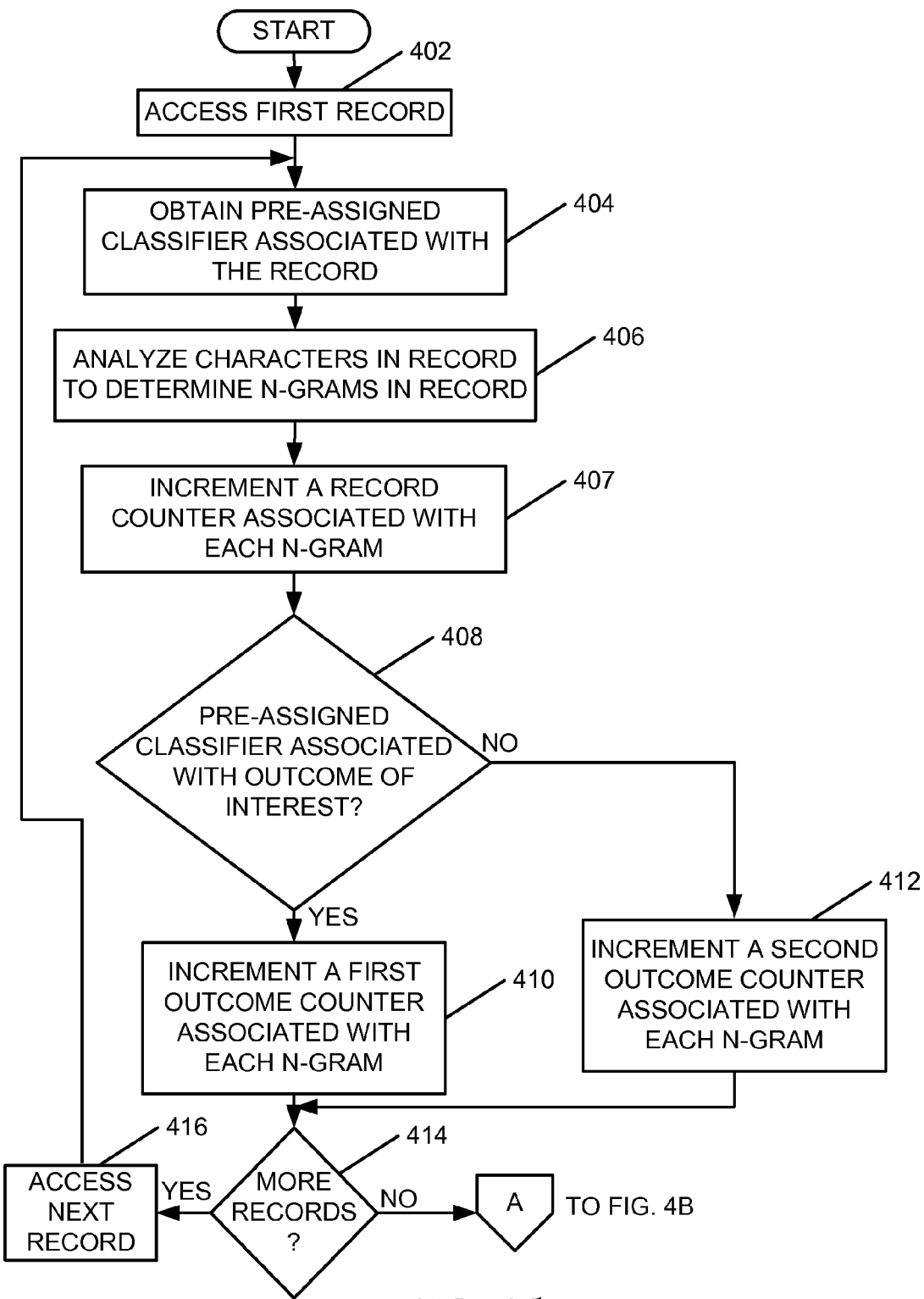
FIGS. 4A and 4B are flowcharts of a second exemplary process that may be performed in another implementation of the complaint classifier generator shown in FIG. 2A.
Figure 4B:
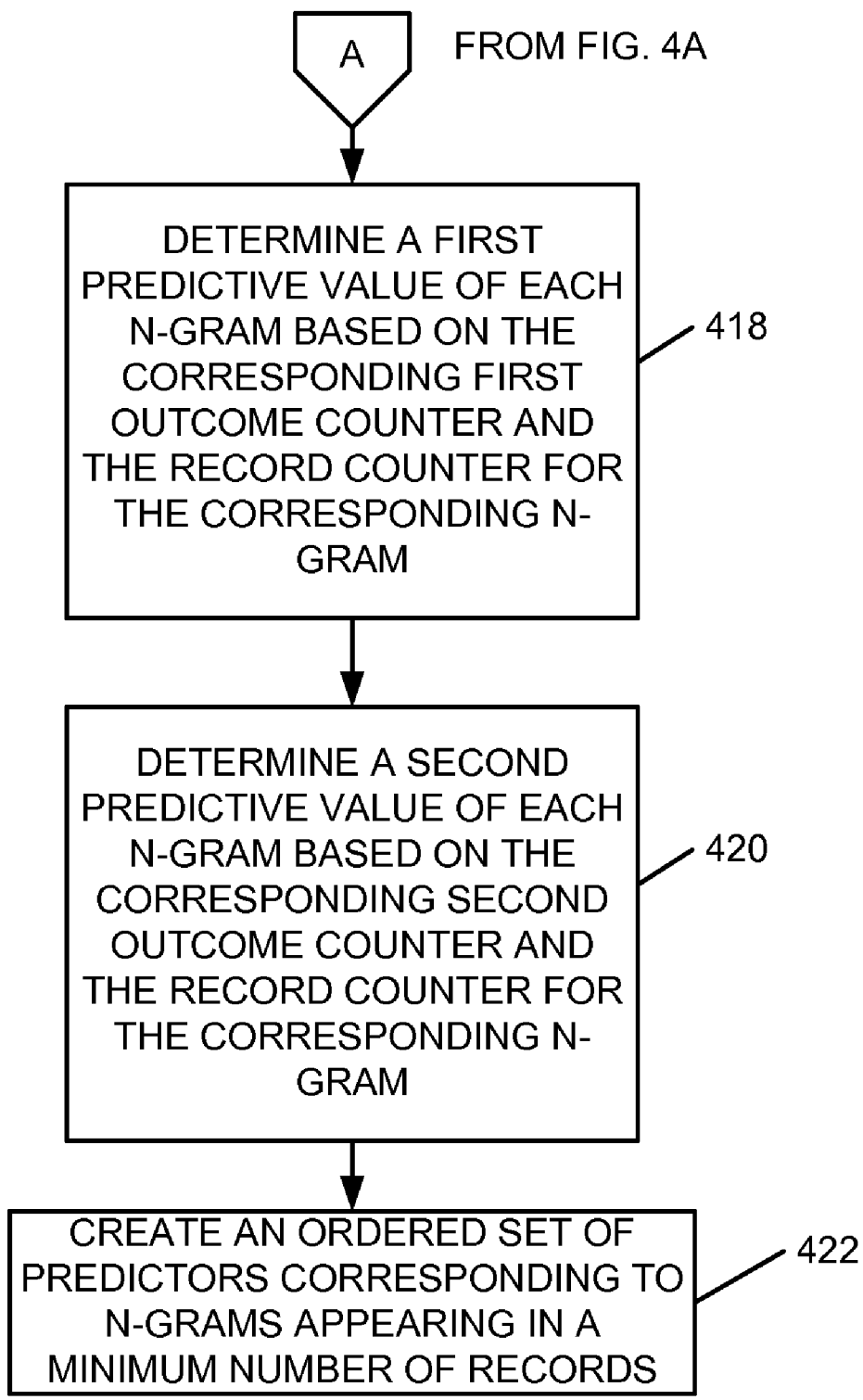

FIGS. 4A and 4B are flowcharts of another exemplary process that may be employed in other implementations of complaint classifier generator 206 consistent with the principles of the invention. In this exemplary process, predictors for two possible outcomes may be generated for predictive model 208. The possible outcomes may be, for example, that a record of a medical complaint is associated with a particular outcome, and that the record of medical complaint is not associated with the particular outcome.

The exemplary process may begin with complaint classifier generator 206 accessing a first one of records of medical complaints 204, which in this process is used as training data (act 402). Next, complaint classifier generator 206 may obtain a classifier corresponding to the record of medical complaints from pre-assigned classifier 202 (act 404). As mentioned above, the classifier from preassigned classifier 202 may be indicative of one or more outcomes.

Complaint classifier generator 206 may then analyze characters in the accessed one of records medical complaints 204 to determine n-grams appearing in the record (act 406). The n-grams may be determined as discussed previously with respect to act 306. Further, complaint classifier generator 206 may store contextual information with the determined n-grams, as previously discussed with respect to FIG. 3. Complaint classifier generator may then increment a record counter associated with each n-gram that appeared in the accessed one of records medical complaints 204 (act 407) in order to keep track of a number of records in which each n-gram appeared.

Next, complaint classifier generator 206 may determine whether the classifier from preassigned classifier 202, corresponding to the record of medical complaint, is associated with the particular outcome (act 408). If the pre-assigned classifier is associated with the particular outcome, then complaint classifier generator 206 may increment a first outcome counter associated with each n-gram determined to appear in the record of medical complaints (act 410).

If, at act 408, complaint classifier generator 206 determines that the pre-assigned classifier is not associated with the particular outcome, then complaint classifier generator 206 may increment a second outcome counter associated with each n-gram that is determined to appear in the record of medical complaint (act 412).

After incrementing the first or the second outcome counters, complaint classifier generator 206 may determine whether there are additional ones of records of medical complaints 204 to analyze (act 414). If there are one or more records of medical complaints 204 to analyze, then complaint classifier generator 206 may access a next one of records of medical complaints 204 and may again perform acts 404-414.

If, at act 414, complaint classifier generator 206 determines that no additional records of medical complaints 204 exist to analyze, then complaint classifier generator 206 may determine a first predictive value of each n-gram based on the corresponding first outcome counter and the record counter for the respective n-gram (FIG. 4B: act 418). The first predictive value may be equal to a value of the corresponding first outcome counter divided by the record counter for the corresponding n-gram (see Eq. 1). The first predictive value may be a value between 0 and 1, inclusive, that represents an expected probability that a record of records of medical complaints 204 is associated with the particular outcome.

Next, complaint classifier generator 206 may then determine a second predictive value of each predictor based on the corresponding second outcome counter and the record counter for the respective n-gram (act 420). The second predictive value may be equal to a value of the corresponding second outcome counter divided by the record counter for the corresponding n-gram (see Eq. 1). The second predictive value may be a value between 0 and 1, inclusive, that represents an expected probability that a record of records of medical complaints 204 is not associated with the particular outcome.

Next, the resulting statistics may be used to create an ordered set of predictors appearing in a minimum number of records (act 422). The ordered set of predictors may be arranged in descending order based on the first or second predictive value corresponding to an n-gram. Each predictor may include an n-gram, a predictive value, and an indication of a particular outcome associated with the respective predictor. As an example, a first predictor of an ordered set may include n-gram "diah", a predictive value of 0.93, and an indication that the predictor is for outcome 1, a second predictor in the ordered set of predictors may include n-gram "naus", a predictive value of 0.88, and an indication that the predictor is for outcome 1, and a third predictor in the ordered set of predictors may include n-gram "feve", a predictive value of 0.75, and an indication that the predictor is for outcome 2. In implementations consistent with the principles of the invention, each n-gram may be associated with only one predictor in the ordered set of predictors, as determined by the highest predictive value associated with the n-gram.

Figure 5A:
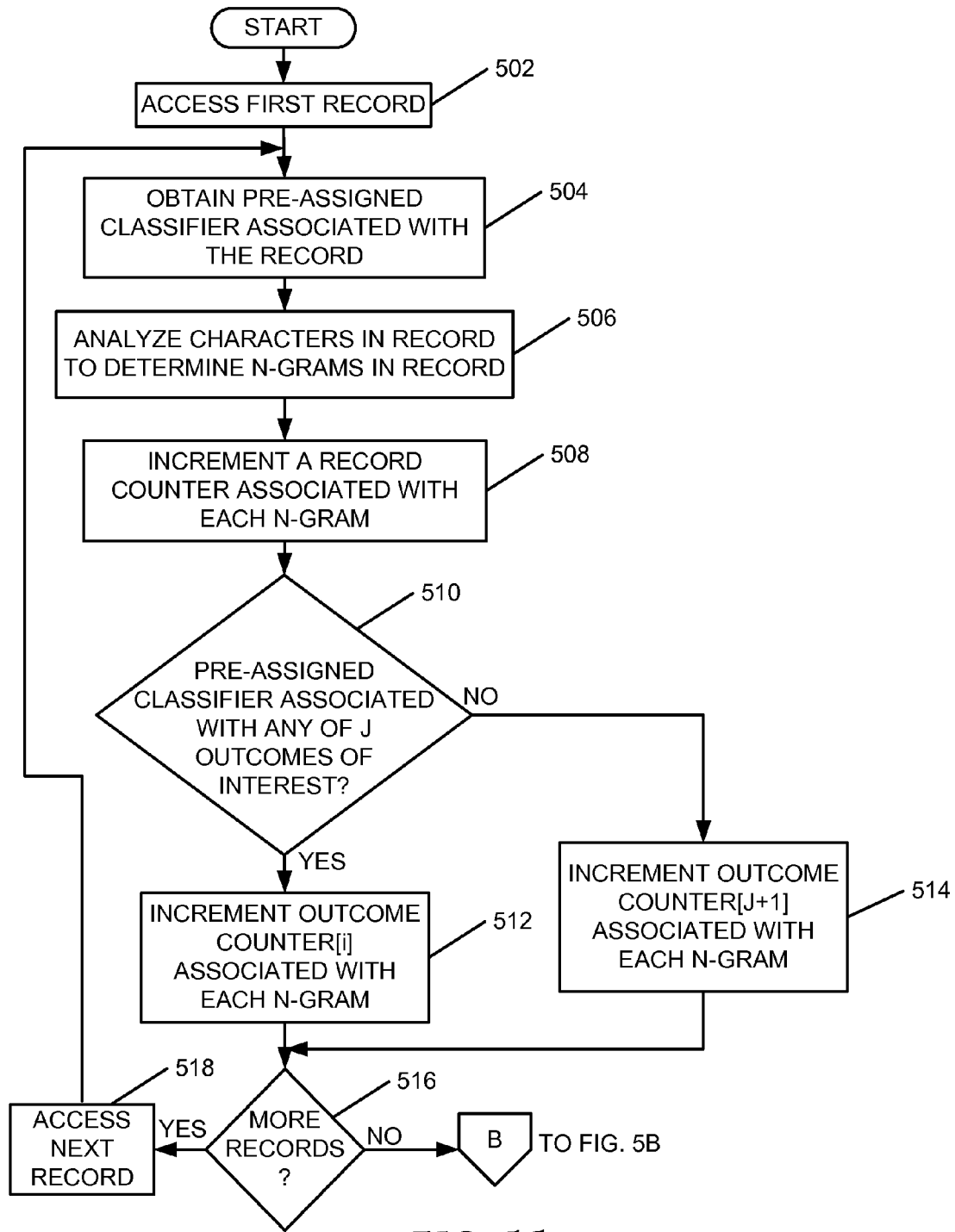
FIGS. 5A and 5B are flowcharts of a third exemplary process that may be performed in yet another implementation of the complaint classifier generator shown in FIG. 2A.
Figure 5B:
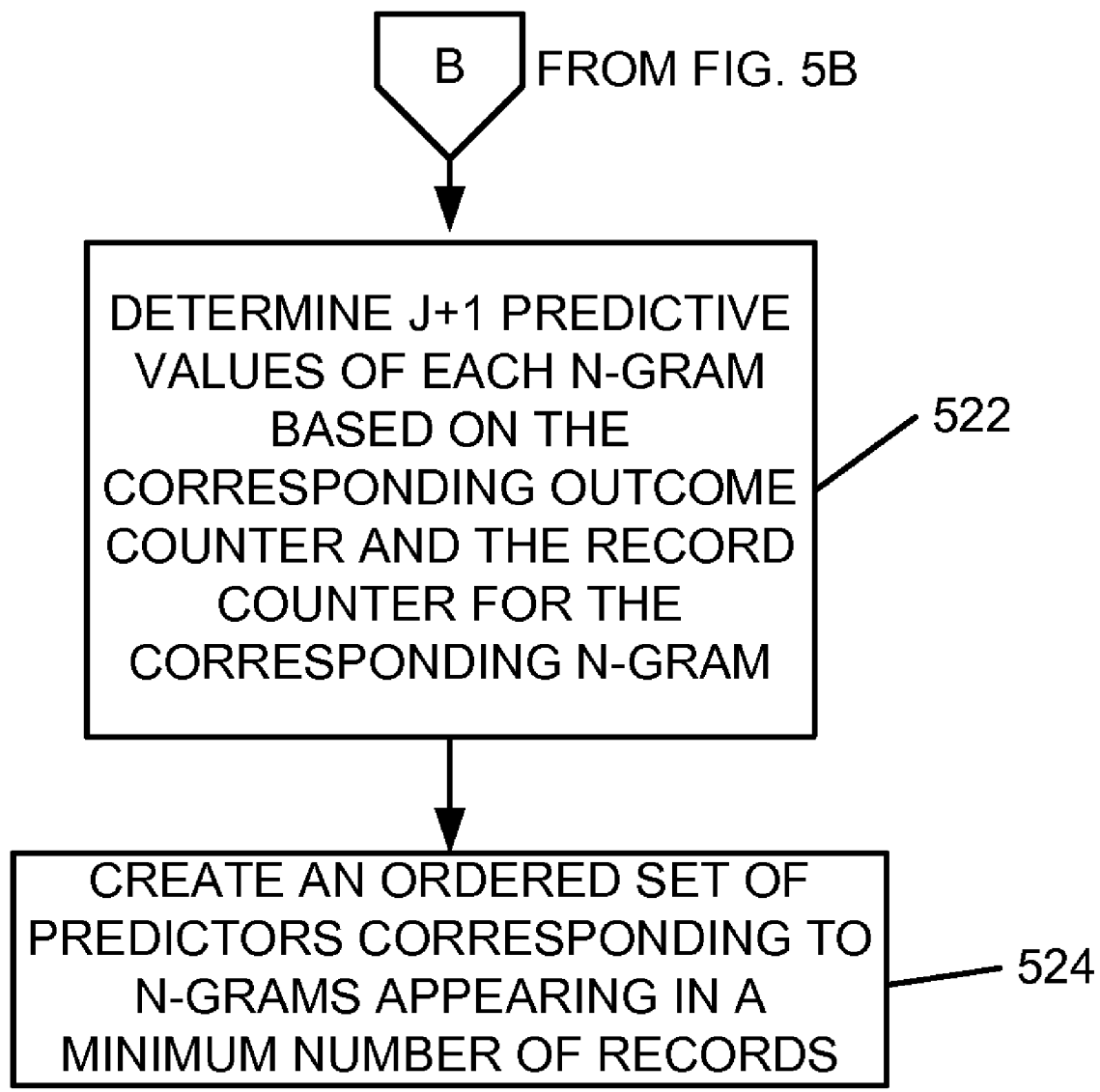

FIGS. 5A-5B are flowcharts that illustrate a third embodiment of complaint classifier 206. In this embodiment, complaint classifier generator 206 may generate an ordered set of predictors for J+1 possible outcomes, where J of the possible outcomes indicate particular outcomes and a $J+1^{st}$ outcome indicates that the outcome is not one of the J possible outcomes.

Complaint classifier generator 206 may begin by accessing a first record of records of medical complaints 204, which may be training data (act 502). Next, complaint classifier generator 206 may obtain a classifier corresponding to the record of medical complaints from pre-assigned classifier 202 (act 504). As mentioned above, the obtained classifier may be indicative of a particular outcome, such as, for example an ICD code assigned by a medical professional upon reviewing a patient's chief complaint data included in a corresponding one of records of medical complaints 204. Alternatively, the obtained classifier may be any data or combination of data items indicative of a particular outcome.

Complaint classifier generator 206 may then analyze characters in the accessed one of records medical complaints 204 to determine n-grams appearing in the record (act 506). Further, complaint classifier generator 206 may store contextual information with the determined n-grams, as discussed with respect to FIG. 3.

Complaint classifier 206 may then increment a record counter associated with each n-gram appearing in the record in order to keep track of a number of records in which each n-gram appears (act 508).

Next, complaint classifier generator 206 may determine whether the pre-assigned classifier corresponding to one of records of medical complaints 204 is associated with one of the J particular outcomes (act 510). If the pre-assigned classifier is associated with one of the J particular outcomes, then complaint classifier generator 206 may increment an element of an outcome counter array associated with each n-gram, which is determined to exist in the record of records of medical complaints 204 (act 512). The particular element of the outcome counter incremented depends on the particular outcome associated with the pre-assigned classifier. For example, when a pre-assigned classifier is determined to be associated with an $i^{th}$ particular outcome, where $1 \leq i \leq J$, then the $i^{th}$ counter in the array of outcome counters with respect to an n-gram may be incremented.

If, at act 510, complaint classifier generator 206 determines that the pre-assigned classifier is not associated with any of the J particular outcomes, then complaint classifier generator 206 may increment an element of the outcome counter array associated with each n-gram, which is determined to exist in the record of records of medical complaint data 204 that is associated with a $(J+1)^{st}$ particular outcome (act 514).

Complaint classifier generator 206 may then determine whether any additional records of medical complaints 204 are to be analyzed (act 516). If more records of medical complaints 204 are to be processed, then complaint classifier generator 206 may access the next record of records of medical complaints 204 (act 518) and acts 504-516 may be repeated.

If complaint classifier generator 206 determines that no additional records of medical complaints 204 are to be analyzed (act 516), then each of the n-grams found in records of medical complaints 204 may be assigned up to J+1 predictive values by calculating a value of a corresponding outcome counter for an outcome divided by a value of a record counter for the corresponding n-gram (see Eq. 1) (act 522).

Complaint classifier generator 206 may then create an ordered set of predictors corresponding to n-grams appearing in a minimum number of records, as described with respect to act 422 (act 524).

Optimizer

Due to a large number of n-grams that complaint classifier generator 206 may generate, it may be desirable to prune or eliminate n-grams (and as a result, predictors) that may not have much predictive value. For example, an n-gram that is associated with a small number of ones of records of medical complaints 204, may in fact be a result of one or more typographical errors. By eliminating such n-grams from predictive model 208, predictive model 208 may become more compact and may result in more accurate and efficient classification of records of medical complaints 228 in an operational environment. Further, because implementations of complaint classifier generator 206 may build an ordered set of predictors based on relative frequencies, it may be desirable to perform pruning of predictors of the ordered set by executing optimizer 210 at least once.

Figure 6A:
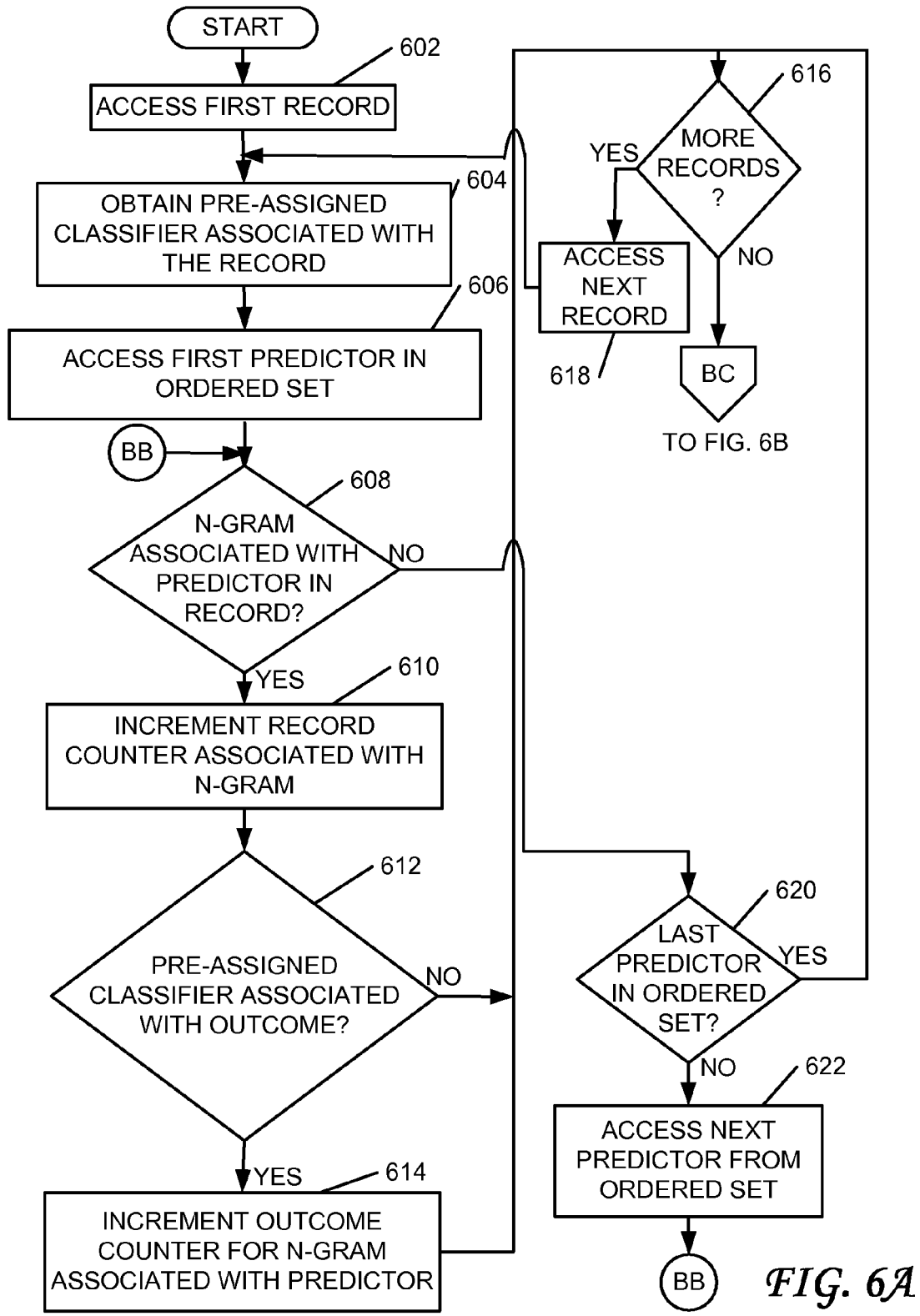
FIGS. 6A and 6B are flowcharts of an exemplary process that may be performed in an implementation of an optimizer shown in FIG. 2A.
Figure 6B:
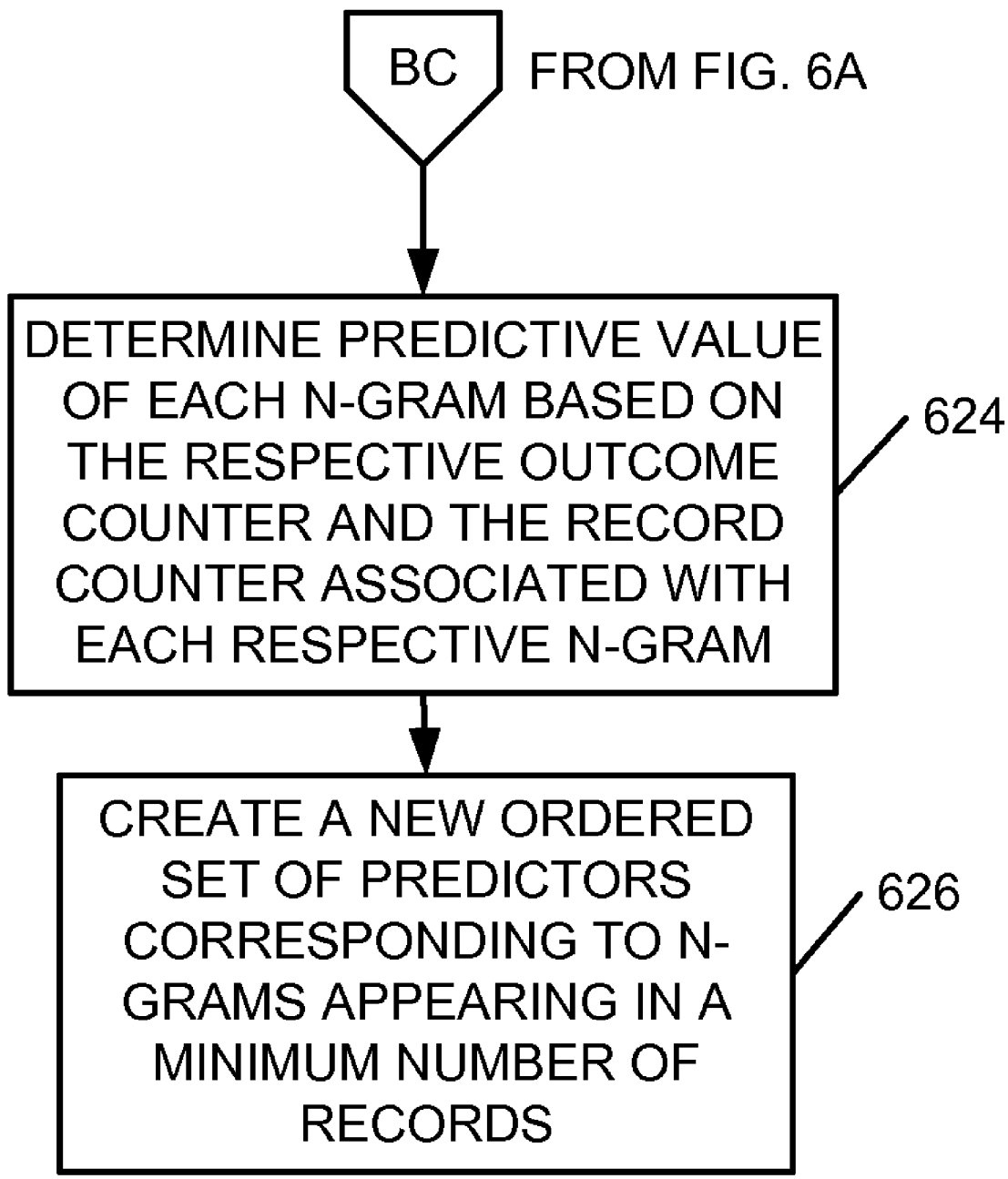

FIGS. 6A and 6B are a flowcharts that illustrate exemplary operation of optimizer 210 for pruning predictors in implementations consistent with the principles of the invention. First, optimizer 210 may access a first record of training data used to create the ordered set of predictors, such as, for example, a first record of medical complaints 204 (act 602). Next, optimizer 210 may obtain a classifier, from preassigned classifier 202, associated with the record (act 604). Optimizer 210 may then access a first predictor in the ordered set of predictors (act 606) and may determine whether the n-gram associated the accessed predictor appears in the record (act 608).

If optimizer 210 determines that the n-gram associated with the predictor appears in the record, then optimizer 210 may increment a record counter associated with the n-gram (act 610). Optimizer 210 may then determine whether the classifier is associated with an outcome-of interest (act 612). If optimizer 210 determines that the classifier is associated with the outcome-of-interest, then optimizer 210 may increment an outcome counter for the n-gram associated with the predictor (act 614). Next, optimizer 210 may determine whether there are additional records to process (act 616). If optimizer 210 determines that there are additional records to process, then a next record is accessed (act 618) and optimizer 210 may repeat acts 604-616.

If, at act 616, optimizer 210 determines that there are no additional records to process, then optimizer 210 may determine the predictive value of each of the n-grams based on the respective outcome counter and the record counter (FIG. 6B: act 624). This may be performed according to the formula of Eq. 1. Optimizer 210 may then create a new ordered set of predictors corresponding to the n-grams, associated with the previous ordered set, that appear in a new minimum number of records (act 626). The new minimum number of records may be configurable and, in some implementations, may be a number, such as, for example, 100 records or another suitable value, or, in other implementations, may be derived from a configurable minimum percentage of records, such as, for example, 5% or another suitable percentage.

If, at act 608, outcome predictor 210 determines that the n-gram associated with the predictor does not appear in the record, then optimizer 210 may determine whether the predictor is the last predictor in the ordered set (FIG. 6A: act 620). If optimizer 210 determines that the predictor is the last predictor in the ordered set, then optimized 210 may proceed to act 616 to determine whether there are more records to process. If optimizer 210 determines that the predictor is not the last predictor in the ordered set (act 620), then optimizer 210 may access a next predictor from the ordered set (act 622) and may perform act 608 to determine whether an n-gram from the next predictor appears in the record.

Optimizer 210 may be executed multiple times with respect to a predictive model, using different values minimum values (minimum number of records or minimum percentage of records) until an optimum size predictive model is built.

Exemplary Processing of Outcome Predictor

Figure 7:
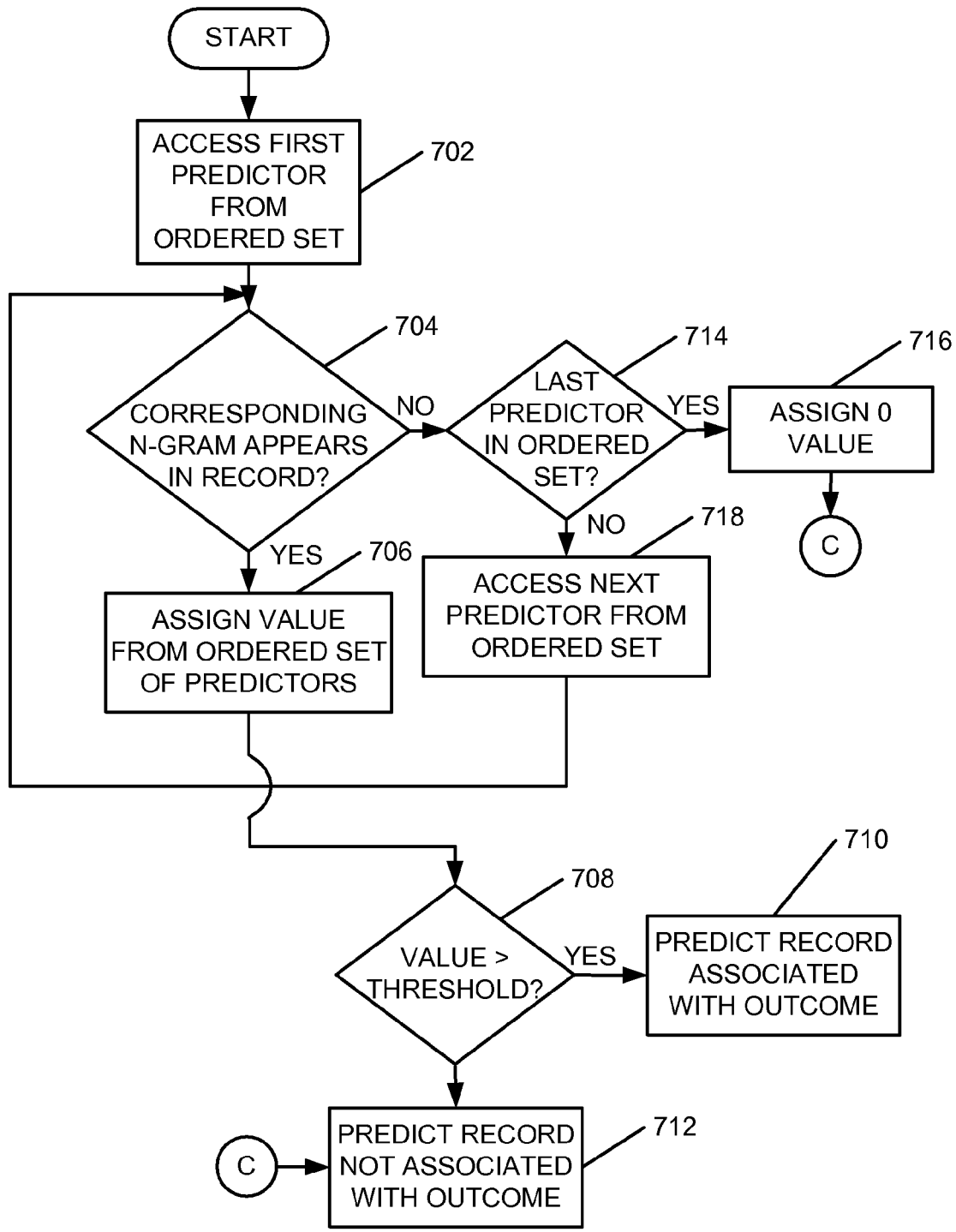
FIG. 7 is a flowchart of an exemplary process that may be performed in an implementation of an outcome predictor shown in FIG. 2B.

FIG. 7 is a flowchart that illustrate exemplary processing of outcome predictor 230, in implementations consistent with the principles of the invention, when processing one of records of medical complaints 228 to produce one or more predictions 232 corresponding to the record. Although the following implementations of outcome predictor 210 may refer to using records of medical complaints 228 as textual input, other information from patients' records may be used as textual input in other implementations.

This particular implementation of outcome predictor may use an ordered set of predictors associated with one outcome. Outcome predictor 230 may begin by accessing a first predictor from the ordered set of predictors (act 702). Each predictor may include information with respect to an n-gram and a predictive value. The ordered set may be arranged in descending order with respect to the predictive value of each of the predictors. Outcome predictor 230 may then perform a text string search to determine whether the n-gram corresponding to the predictor appears in the current one of the record of medical complaints 228 (act 704). If the n-gram appears in the current one of the record of medical complaints 228, then outcome predictor 230 may assign the predictive value from the predictor to be an expected probability of the outcome (act 706) and may determine whether the predictive value is greater than a threshold (act 708). If the predictive value is greater than the threshold, then outcome predictor 230 may provide output indicating that the current one of the record of medical complaints 228 is associated with the outcome (act 710). If the predictive value is not greater than the threshold, then outcome predictor 230 may provide output indicating that the current one of the record of medical complaints 228 is not associated with the outcome (act 712).

If outcome predictor 230 determines that the n-gram associated with the predictor does not appear in the record (act 704), then outcome predictor 230 may determine whether the predictor is the last predictor in the ordered set (act 714). If the predictor is the last one in the ordered set, then outcome predictor 230 may assign a value of 0 to be the expected probability of the outcome, indicating that the expected probability of the current one of record of medical complaints 228 is 0 (act 716). Outcome predictor may then proceed to act 712 to predict that the current one of record of medical complaints 228 is not associated with the outcome (act 712).

If outcome predictor 230 determines that the predictor is not the last predictor in the ordered set of predictors, then outcome predictor may access a next predictor from the ordered set of predictors (act 718) and may then proceed to act 704 to determine whether the corresponding n-gram appears in the current one of records of medical complaints 228.

Figure 8:
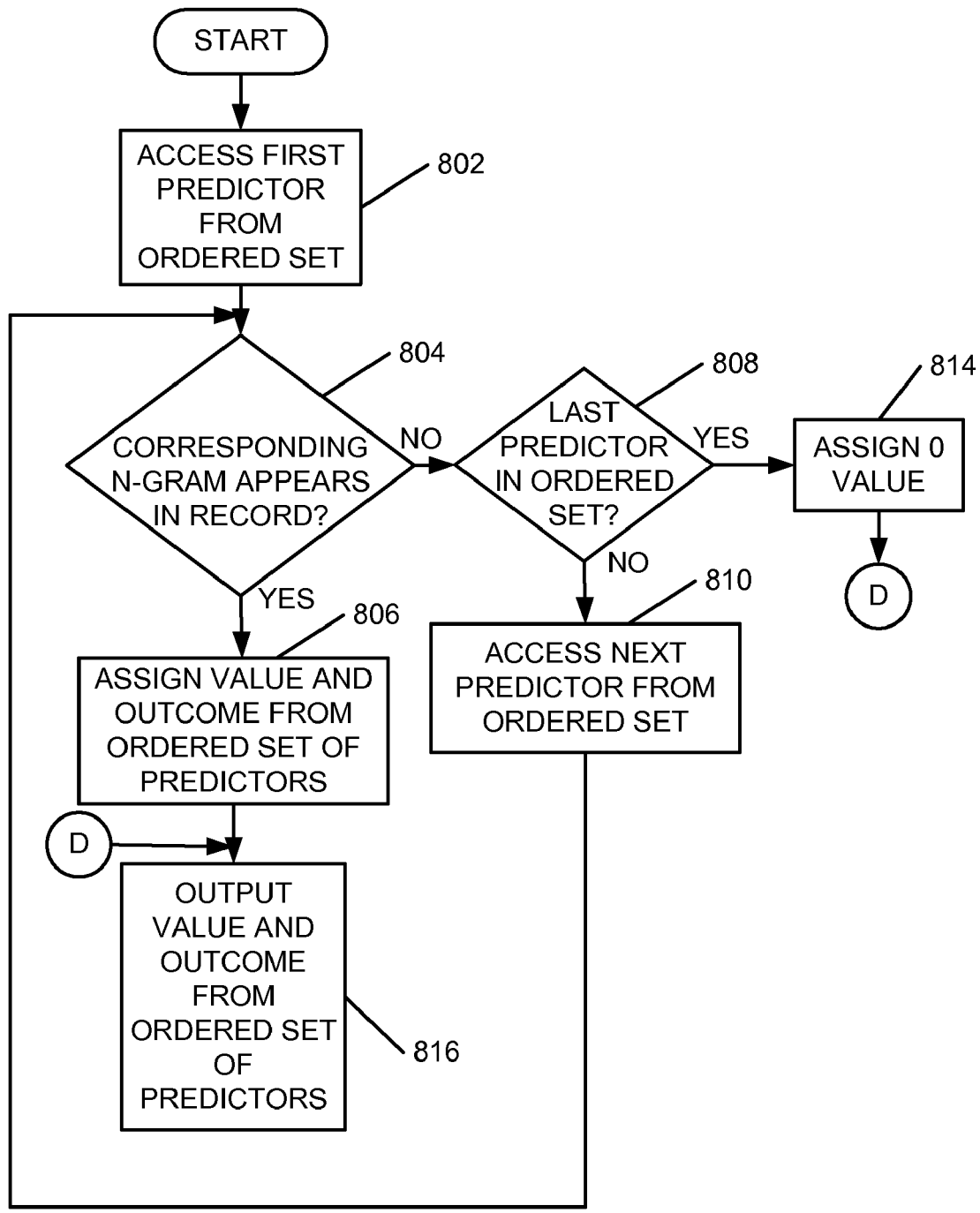
FIG. 8 is a flowchart of another exemplary process that may be performed in another implementation of the outcome predictor of FIG. 2B.

FIG. 8 is a flowchart that illustrate processing in another implementation of outcome predictor 230 consistent with the principles of the invention. In this implementation, predictive model 208 may have an ordered set of predictors for multiple outcomes. For example, there may be J+1 possible outcomes, in which J of the outcomes may be particular outcomes and a J+1$^{st}$ outcome may be any outcome other than the J particular outcome. In one implementation consistent with the principles of the invention, J may be 10.

Outcome predictor 230 may begin by accessing a first predictor from the ordered set of predictors (act 802). Each predictor may include information with respect to an n-gram, a predictive value, and an outcome to which the predictor pertains. The ordered set may be arranged in descending order with respect to the predictive value of each of the predictors. Outcome predictor 230 may then perform a text string search to determine whether the n-gram corresponding to the predictor appears in the current one of the record of medical complaints 228 (act 804). If the n-gram appears in the current one of the record of medical complaints 228, then outcome predictor 230 may assign the predictive value from the predictor to be an expected probability of an outcome and may assign a value indicating to which one of the possible outcomes the predictor pertains (act 806). Outcome predictor 230 may then proceed to act 816 to output the value and outcome from the ordered set or predictors.

If outcome predictor 230 determines that the n-gram associated with the predictor does not appear in the record (act 804), then outcome predictor 230 may determine whether the predictor is the last predictor in the ordered set (act 808). If the predictor is the last one in the ordered set, then outcome predictor 230 may assign a value of 0 to be the expected probability of all of the outcomes (act 814). Outcome predictor 230 may then output the highest predictive value and corresponding outcome indication from the ordered set of predictors (act 816).

Although the exemplary processing of FIGS. 7 and 8 employ one ordered set of predictors to produce a most likely outcome, alternative implementations of outcome predictor 230 may use multiple ordered sets of predictors, where each of the ordered sets of predictors may pertain to different outcomes, to produce multiple outputs.

Miscellaneous

Figure 9:
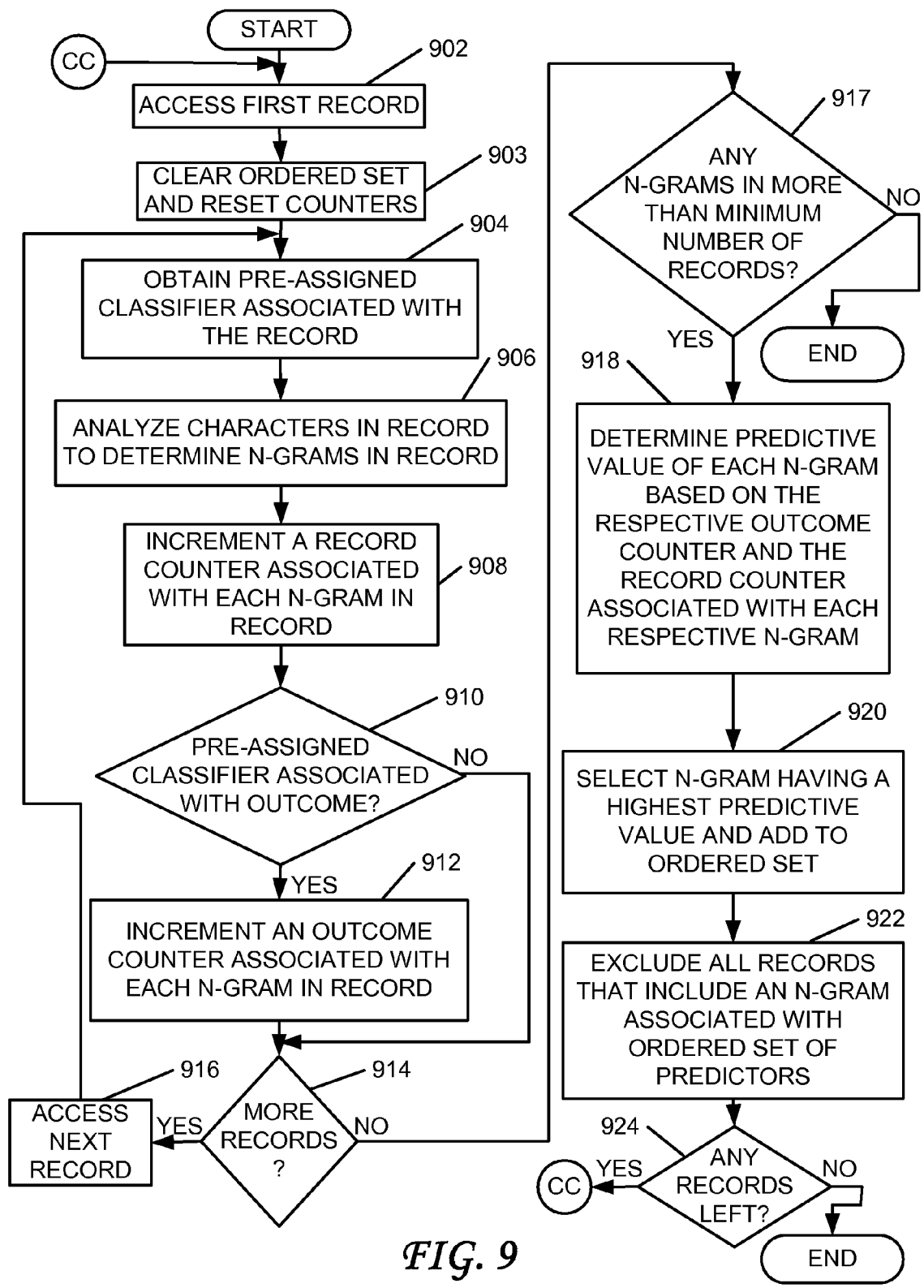
FIG. 9 is a flowchart of an exemplary process that may be performed in another implementation of the complaint classifier generator of FIG. 2A.

The above described implementations of complaint classifier generator 206 may calculate predictive values based on a relative frequency of an n-gram appearing in records associated with an outcome of interest and based on a total number of records in which the n-gram appears. Another implementation of complaint classifier 206, consistent with the principles of the invention, is illustrated with reference to the flowchart of FIG. 9. In this implementation, complaint classifier generator 206 may use a stepwise variable selection approach.

Complaint classifier generator 206 may begin by accessing a first record from training data, such as, for example, records of medical complaints 204 (act 902). Classifier complaint generator 206 may then clear, or blank-out, the ordered set of predictors and may reset counters, such as record counters and outcome counters (act 903). Next, complaint classifier 206 may obtain a classifier associated with the accessed record from preassigned classifier 202 (act 904). Complaint classifier 206 may then analyze characters in the record to determine all of the n-grams that appear in the record (act 906). This may be performed as described with respect to the implementation of FIG. 3. Complaint classifier 206 may then increment a record counter associated with each n-gram that appears in the record (act 908).

Next, complaint classifier 206 may determine whether the record is associated with an outcome-of-interest based on the associated classifier from preassigned classifier 202 (act 910). If complaint classifier 206 determines that the classifier is associated with the outcome-of-interest, then complaint classifier 206 may increment an outcome counter associated with each of the n-grams that appear in the record (act 912). Complaint classifier 206 may then determine whether there are more records to process (act 914). If there are more records to process, then complaint classifier 206 may access a next record (act 916) and may repeat acts 904-914. If complaint classifier 206 determines that there are no additional records to process (act 914), then complaint classifier 206 may determine whether any of the n-grams found in the records appear in more than a minimum number of records (act 917). If none of the n-grams found in the records appear in more than a minimum number of records, then the process is completed.

If, at act 917, complaint classifier 206 determines that there are n-grams that appear in more than a minimum number of the records then complaint classifier 206 may determine a predictive value of each of the n-grams that appeared in the records more than the minimum number of times based on the outcome counter and the record counter associated with respective n-grams. The predictive value may be calculated according to Eq. 1.

Next, complaint classifier 206 may select an n-gram having a highest calculated predictive value and add a predictor to the ordered set of predictors that corresponds to this n-gram and predictive value (act 920). Complaint classifier 206 may then exclude all of the records that include an n-gram associated with the ordered set of predictors (act 922). Complaint classifier 206 may then determine whether any records exist, after excluding ones of the records that include n-grams that are associated with the ordered set of predictors (act 924). If no records exist, then the process is completed. Otherwise, complaint classifier 206 may repeat acts 902-924.

In an alternative implementation of complaint classifier 206, while performing act 920, complaint classifier 206 may check the predictive value of the selected n-gram before adding a new predictor to the ordered set of predictors. If the predictive value is less than a predetermined amount, such as, for example, 0.01, then the process may end. In this alternative, implementation, complaint classifier generator 206 will not add predictors to the ordered list when the predictor has a very small predictive value.

CONCLUSION

The above-described embodiments are exemplary and are not limiting with respect to the scope of the invention. Although the above-described embodiments discuss either creating a predictive model from records of medical complaints 204, or using the created predictive models to predict or forecast an outcome associated with records of medical complaints 228, other types of records may be used in other embodiments to generate predictive models and to forecast one or more outcomes. Further, embodiments of the invention may not be limited to any particular language, but may be used with records of any language to create predictive models and to forecast one or more outcomes.

Embodiments within the scope of the present invention may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other embodiments of the invention may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination thereof through a communications network. In a distributed computing environment, program modules may be located in both local and remote memory storage devices.

Although the above description may contain specific details, they should not be construed as limiting the claims in any way. Other configurations of the described embodiments of the invention are part of the scope of this invention.

For example, hardwired logic may be used in implementations instead of processors, or one or more application specific integrated circuits (ASICs) may be used in implementations consistent with the principles of the invention. Further, implementations consistent with the principles of the invention may have more or fewer acts than as described, or may implement acts in a different order than as shown. Accordingly, the appended claims and their legal equivalents should only define the invention, rather than any specific examples given.

We claim:

1. A method for forecasting whether a record of data for an individual is associated with an outcome, the method comprising:

determining whether an n-gram associated with one of a plurality of predictors matches an n-gram included in the record of data; and predicting whether the record of data is associated with the outcome based on a value assigned to the one of the plurality of predictors, when the n-gram associated with the one of the plurality of predictors matches the n-gram in the record of data.

2. The method of claim 1, wherein determining whether an n-gram associated with one of a plurality of predictors matches an n-gram included in the record of data, further comprises:

searching the record of data for an n-gram that matches the n-gram associated with the one of the plurality of predictors;

obtaining data pertaining to a next predictor, such that the next predictor is treated as the one of the plurality of predictors and repeating the previous act of searching the record of data for an n-gram, when the record of data does not include an n-gram that matches the n-gram associated with the one of the plurality of predictors;

providing a value associated with the one of the plurality of predictors having a matching associated n-gram as the value assigned to the one of the plurality of predictors.

3. The method of claim 2, wherein the plurality of predictors is included in an ordered set of predictors that is arranged in a descending order based on a respective value associated with each of the plurality of predictors.

4. The method of claim 2, wherein the n-grams associated with the plurality of predictors include contextual information.

5. The method of claim 1, further comprising:

generating the plurality of predictors based, at least in part, on a plurality of records of data used as training data and associated data indicative of one or more outcomes.

6. The method of claim 3, wherein determining whether an n-gram associated with one of a plurality of predictors matches an n-gram included in the record of data further comprises:

comparing the n-gram included in the record of data with the n-gram associated with a predictor from the ordered set of predictors, stopping the comparing of the n-gram included in the record of data when the n-gram included in the record of data matches the n-gram associated with the one of the plurality of predictors from the ordered set of predictors, and comparing the n-gram included in the record of data with an n-gram associated with a next predictor from the ordered set of predictors when the n-gram doesn't match the n-gram associated with the predictor from the ordered set of predictors.

7. A machine-readable medium having recorded thereon a plurality of instructions for at least one processor, the machine-readable medium comprising:

instructions for determining a plurality of n-grams included in a record of data;

instructions for incrementing a respective record counter associated with each of the plurality of n-grams included in the record of data;

instructions for determining whether the record of data is associated with an outcome of interest based, at least in part, on data associated with the record of data indicative of one or more outcomes;

instructions for incrementing a respective outcome counter associated with each of the plurality of n-grams included in the record of data when the record of data is determined to be associated with the outcome of interest;

instructions for repeating the previous four sets of instructions for each of a plurality of records of data; and instructions for assigning a value to each of the n-grams based on a value of the respective outcome counter and a value of a corresponding record counter for the respective n-gram.

8. The machine-readable medium of claim 7, further comprising:

instructions for incrementing a second outcome counter associated with each of the plurality of n-grams included in the record of data when the record of data is determined not to be associated with the outcome of interest; and instructions for assigning a second value to each of the n-grams based on a value of a respective second outcome counter and a value of a corresponding record counter for the respective n-gram.

9. The machine-readable medium of claim 7, wherein the instructions for determining a plurality of n-grams included in a record of data further comprises:

instructions for determining all groupings of n consecutive ones of characters included in the record of data, where none of the n consecutive ones of the characters include a delimiter between any of the n consecutive ones of the characters;

instructions for determining all groupings of less than n consecutive ones of characters having a delimiter only at a beginning and an ending of the less than n consecutive ones of the characters; and instructions for generating the plurality of n-grams from the groupings of n consecutive ones of the characters and the groupings of less than n consecutive ones of the characters having a delimiter only at the beginning and the ending of each of the less than n consecutive ones of the characters.

10. The machine-readable medium of claim 7, further comprising instructions for including contextual information with the determined plurality of n-grams.

11. The machine-readable medium of claim 7, further comprising:

instructions for pruning ones of the predictors associated with an n-gram that occurs in less than a predetermined number of the records of data or in less than a predetermined percentage of the records of data.

12. A processing device comprising:

at least one processor;

a storage component having stored therein a plurality of instructions; and a communications interface arranged to permit communications between the at least one processor and the storage component, wherein the at least one processor is arranged to:
   determine a plurality of n-grams included in a record of data,
   increment a respective record counter associated with each of the plurality of n-grams included in the record of data,
   determine whether the record of data is associated with an outcome of interest based, at least in part, on data associated with the record of data indicative of one or more outcomes,
   increment a respective outcome counter associated with each of the plurality of n-grams included in the record of data when the record of data is determined to be associated with the outcome of interest,
   repeat the previous four acts for each of a plurality of records of data, and
   assign a value to each of the n-grams based on a value of the respective outcome counter and a value of a corresponding record counter for the respective n-gram.

13. The processing device of claim 12, wherein the at least one processor is further arranged to:
   increment a second outcome counter associated with each of the plurality of n-grams included in the record of data when the record of data is determined not to be associated with the outcome of interest.

14. The processing device of claim 12, wherein the at least one processor is further arranged to determine a plurality of n-grams included in a record of data by:
   determining all groupings of n consecutive ones of characters included in the record of data, where none of the n consecutive ones of the characters include a delimiter between any of the n consecutive ones of the characters;
   determining all groupings of less than n consecutive ones of the characters having a delimiter only at a beginning and an ending of the less than n consecutive ones of the characters; and
   generating the plurality of n-grams from the groupings of n consecutive ones of the characters and the groupings of less than n consecutive ones of the characters having a delimiter only at the beginning and the ending of each of the less than n consecutive ones of the characters.

15. The processing device of claim 12, wherein the at least one processor is further arranged to include contextual information with the determined plurality of n-grams.

16. The processing device of claim 12, wherein the at least one processor is further arranged to prune ones of the predictors that occur in less than a predetermined number of the records of data or in less than a predetermined percentage of the records of data.

17. A processing device for predicting whether a record of data for an individual is associated with an outcome, the processing device comprising:
   means for determining whether an n-gram associated with one of a plurality of predictors matches an n-gram included in the record of data; and
   means for predicting whether the record of data is associated with the outcome based on a value assigned to the one of the plurality of predictors, when the n-gram associated with the one of the plurality of predictors matches the n-gram in the record of data.

18. The processing device of claim 17, wherein the means for determining whether an n-gram associated with one of a plurality of predictors matches an n-gram included in the record of data, further comprises:
   means for searching the record of data for an n-gram that matches the n-gram associated with the one of the plurality of predictors;
   means for obtaining data pertaining to a next predictor, such that the next predictor is treated as the one of the plurality of predictors and repeating the previous act of searching the record of data for an n-gram, when the record of data does not include an n-gram that matches the n-gram associated with the one of the plurality of predictors;
   means for providing a value associated with the one of the plurality of predictors having a matching associated n-gram as the value assigned to the one of the plurality of predictors.

19. The processing device of claim 18, wherein the plurality of predictors is included in an ordered set of predictors that is arranged in a descending order based on a respective value associated with each of the plurality of predictors.

20. The processing device of claim 19, wherein the n-grams associated with the plurality of predictors include contextual information.

21. The processing device of claim 17, further comprising:
   means for generating the plurality of predictors based, at least in part, on a plurality of records of data and associated data indicative of one or more outcomes.

22. The processing device of claim 17, further comprising:
   means for determining whether an n-gram included in the record of data matches an n-gram associated with one of a plurality of predictors arranged as an ordered set of predictors, wherein the means for determining whether an n-gram included in the record of data matches an n-gram associated with one of a plurality of predictors arranged as an ordered set of predictors further comprises:
      means for comparing the n-gram included in the record of data with the n-gram associated with a predictor from the ordered set of predictors,
      means for stopping the comparing of the n-gram included in the record when the n-gram included in the record of data matches the n-gram associated with the one of the plurality of predictors from the ordered set of predictors, and
      means for comparing the n-gram included in the record of data with a next predictor from the ordered set of predictors when the n-gram doesn't match the n-gram associated with the predictor from the ordered set of predictors.

* * * * *